United States Patent [19]

Veth et al.

[11] 4,036,211
[45] July 19, 1977

[54] TEMPERATURE, PULSE AND RESPIRATION DETECTION APPARATUS

[75] Inventors: George J. Veth, Fairfield; Douglas G. Noiles, New Canaan, both of Conn.

[73] Assignee: United States Surgical Corporation, Baltimore, Md.

[21] Appl. No.: 566,073

[22] Filed: Apr. 8, 1975

[51] Int. Cl.² .............................................. A61B 5/00
[52] U.S. Cl. ................................... 128/2 R; 128/2 H; 128/2.05 P
[58] Field of Search ............ 128/2 H, 2.05 R, 2.05 P, 128/2.08; 73/344, 362.8

[56] References Cited

U.S. PATENT DOCUMENTS

| | | | |
|---|---|---|---|
| 1,942,516 | 1/1934 | Noyes, Jr. .................................. 136/4 |
| 3,081,765 | 3/1963 | Kompelien .................................. 128/2 |
| 3,103,214 | 9/1963 | Smith .................................. 128/2.05 P |
| 3,107,664 | 10/1963 | Smith .................................. 128/2.05 P |
| 3,139,086 | 6/1964 | Botsch et al. .................................. 128/2.05 P |
| 3,215,265 | 11/1965 | Welin-Berger .................................. 206/63.2 |
| 3,359,975 | 12/1967 | Sherman .................................. 128/2.05 P |
| 3,513,832 | 5/1970 | Klemm et al. .................................. 128/2.05 |
| 3,531,992 | 10/1970 | Moore .................................. 73/359 |
| 3,540,432 | 11/1970 | Ayre .................................. 128/2 B |
| 3,572,322 | 3/1971 | Wade .................................. 128/2.06 E |
| 3,593,704 | 7/1971 | Schwab .................................. 128/2.05 |
| 3,645,133 | 2/1972 | Simeth et al. ........ 128/DIG. 29 UX |
| 3,721,001 | 3/1973 | Crosby et al. .................................. 29/612 |
| 3,839,039 | 10/1974 | Suzuki et al. .................................. 96/38.3 |
| 3,851,529 | 12/1974 | Andrews et al. .................................. 73/362.8 |
| 3,884,219 | 5/1975 | Richardson et al. .................................. 128/2 R |
| 3,893,452 | 7/1975 | Birnbaum .................................. 128/2.05 A |
| 3,916,877 | 11/1975 | Beckman .................................. 128/2.05 R |
| 3,935,744 | 2/1976 | Beckman .................................. 73/361 |
| 3,999,537 | 12/1976 | Noiles .................................. 128/2 R |

OTHER PUBLICATIONS

Gundersen (I) "Reg. of Breathing Rate with Twin Thermocouples," Proceedings of the 1st Nordic Meeting on Med. and Biol. Eng'g, pp. 158-160, Jan. 1970.
Gundersen (II), "Therm. Amp. for Temp." Med. and Biol. Eng., vol. 10, pp. 564-566, Dec. 1971.

*Primary Examiner*—William H. Grieb
*Attorney, Agent, or Firm*—Fleit & Jacobson

[57] ABSTRACT

A temperature, pulse and respiration detector having a non-disposable sensor and a disposable cover. The sensor comprises a probe having a thermistor mounted at one end for insertion into the body to sense temperature. The sensor also comprises a thermistor spaced from the end of the probe and housed within the body of the sensor for sensing respiration. Pulse is sensed by a photoelectric detector mounted in the sensor body. The disposable cover has at least one opening which associates with the respiration-sensing thermistor so that the thermistor is exposed to respiration and at least one radiation transmitting portion which associates with the photoelectric detector. In normal use, the patient places the probe in his mouth while holding the sensor in his hand so that his finger is over the photoelectric detector. The patient's temperature is sensed by the thermistor in his mouth, his respiration by the respiration-sensing thermistor in the sensor body and his pulse rate derived from the changes in the radiation transmission characteristics of his finger sensed by the photoelectric detector.

36 Claims, 13 Drawing Figures

TEMPERATURE, PULSE AND RESPIRATION DETECTION APPARATUS

BACKGROUND OF THE INVENTION

This invention relates to a temperature, pulse and respiration detector. More particularly, this invention relates to a combined temperature, pulse and respiration detector in which a patient's temperature can be sensed simultaneously with his pulse and respiration rates.

It is well known to use a temperature sensor such as a thermistor to sense temperature or to detect respiration. It is also well known to detect pulse rate using the photoelectric measurement of changes in the radiation transmission characteristics of tissue through which blood is circulating. One photoelectric method of pulse rate detection is disclosed in U.S. Pat. No. 3,139,086.

Techniques have been only recently developed for simultaneously sensing temperature, pulse rate and/or respiration by means suitable for economic wide spread use, as for instance, in hospital wards. These known temperature, pulse and/or respiration detectors comprise a disposable probe with a thermopile mounted thereon and are disclosed in commonly assigned application Ser. No. 409,637, filed Oct. 25, 1973 for TEMPERATURE, PULSE AND RESPIRATION DETECTOR, by Douglas G. Noiles, one of the co-inventors herein. These detectors represent a marked advance over the state of the art but have some disadvantages including the mounting of the temperature and/or respiration sensors on the disposable probe. For reasons of economy, it would be desirable to have a detector for simultaneously detecting temperature, pulse and respiration in which the sensor is non-disposable and adapted to associate with a disposable cover so that the sensor can be used in a hygienic manner.

It is known to determine respiratory activity by detecting the flow of air through the nostrils. A typical pneumograph employs a thermistor placed in the outer nasal passage to detect the temperature change of the thermistor due to the cooling effect of the flow of inspired and expired air. It is also known to place the thermistor in the mouth or in a position to detect flow from either the nose or the mouth. However, if the thermistor is placed in the outer nasal passagge or mouth, the thermistor cannot be re-used without being sterilized. Accordingly, there is a need in the art for a detector for detecting the flow of respiratory air which is reusable without being sterilized after each use. Furthermore, a suitable detector is yet to be developed for housing the respiration sensor and for directing air flow to the sensor.

Known methods and apparatus for photoelectrically measuring the pulse rate by detecting changes in the radiation transmission characteristics of blood carrying tissue such as disclosed in U.S. Pat. No. 3,139,086 employ a detector in which the patient's thumb, for example, is placed over the end of a detector containing a suitable light source and photocell. In these devices, no provision is made to avoid the transmission of bacteria from one patient to another, nor is the apparatus adapted to be used for the simultaneous detection of oral temperature, pulse and respiration. Accordingly, problems of hygiene may arise in a hospital environment from the use of these devices and their applicability is limited.

SUMMARY OF THE INVENTION

An object of the present invention is to provide a detector for sensing temperature, pulse and/or respiration.

Another object of the present invention is to provide a detector in which the temperature, pulse and respiration detectors are members of a unitary non-disposable sensor.

Still another object of the present invention is to provide a detector for housing a respiration sensor which is suitably shaped to direct exhaled respiration air to the sensor.

Yet another object of the present invention is to provide a disposable cover for a respiration sensor shaped to direct respiratory air to the sensor.

Still another object of the present invention is to provide a disposable cover having at least one opening for transmitting exhaled respiratory air to the sensor.

A still further object of the present invention is to provide a disposable cover for a photoelectric pulse detector having a radiation transmitting portion for transmitting radiation to and from the detector.

Yet another object of the present invention is to provide a disposable cover having a heat-transmitting portion adapted to associate with an oral temperature sensor.

A temperature, pulse and respiration detector is provided in accordance with the present invention having a non-disposable sensor and a disposable cover. The sensor comprises a probe having a thermistor mounted at one end for insertion into the body to sense temperature. The sensor also comprises a thermistor spaced from the end of the probe for sensing respiration and photoelectric detector for sensing pulse.

In normal use, the patient holds the sensor in his hand so that his finger is over the photoelectric detector and places the probe in his mouth. The patient's temperature is sensed by the temperature-sensing thermistor in his mouth, his respiration by the respiration-sensing thermistor which is exposed to his exhaled respiratory air flow and his pulse rate derived from the changes in the radiation transmission characteristics of his finger sensed by the photoelectric pulse detector.

The disposable cover is shaped to direct the respiratory air to the respiration thermistor and preferably has at least one opening which associates with the respiration thermistor so that the thermistor is exposed to nasal exhaled respiration. The disposable cover also has a radiation transmitting portion which associates with the photoelectric detector. The disposable cover has a flexible heat-transmitting portion for covering the oral temperature-sensing thermistor. Preferably, the inside of the tip of the flexible heat-transmitting portion of the disposable cover is moistened with a heat conducting fluid to provide better heat transfer between the cover and the temperature-sensing thermistor. This fluid also serves as a lubricant to facilitate the insertion of the temperature sensing portion of the probe.

DESCRIPTION OF THE PREFERRED EMBODIMENTS

Referring to FIGS. 1-4, the detector comprises sensor 12 which includes housing 14 and probe 16. Base 18, top 20 and center plate 22 of housing 14 are preferably fabricated from a rigid thermoplastic such as an acrylonitrile-butadiene-styrene terpolymer and are secured together by adhesive. Base 18 has channel 24 formed at its forward end for receiving the rear end of probe 16. Probe 16 is preferably offset from the longitudinal center line of housing 14 in order to be more easily inserted under the tongue of a patient. However, probe 16 can also have its axis coincide with the longitudinal center line of housing 14 as shown in dotted lines in FIG. 1. Probe 16 is secured in channel 24 by adhesive or other suitable means and is also held in place by the bottom surface of center plate 22.

Top 20 of housing 14 houses photoelectric pulse detector 26 which comprises light bulb 28 and photocell 30. Light bulb 28 is housed in an appropriately shaped opening (not shown) in ring 32 which is made of a suitable radiation transmitting material such as an acrylic sold under the trademark Plexiglas or Lucite. Radiation-transmitting ring 32 diffuses the light and heat transmitted from detector 26 to the patient's finger. Pulse detection is preferably accomplished using electromagnetic energy having infra-red wave lenghts. In the embodiment shown in FIGS. 1-4, photoelectric pulse detector 26 is mounted directly in resilient material 34 made of a suitable rubber such as silicone rubber or Neoprene which is secured such as by the use of adhesive in opening 36 formed in top 20. The function of resilient material 34 is to cushion the portion of housing 14 gripped by the patient so that the patient will not grip the housing so tightly that the normal flow of blood through the digit being monitored is restricted. Resilient material 34 extends from the top surface of top 20 to just above center plate 22 of housing 14 so that the finger of the patient directly contacts the resilient material.

Figures 3, 4, 6A, 6B:
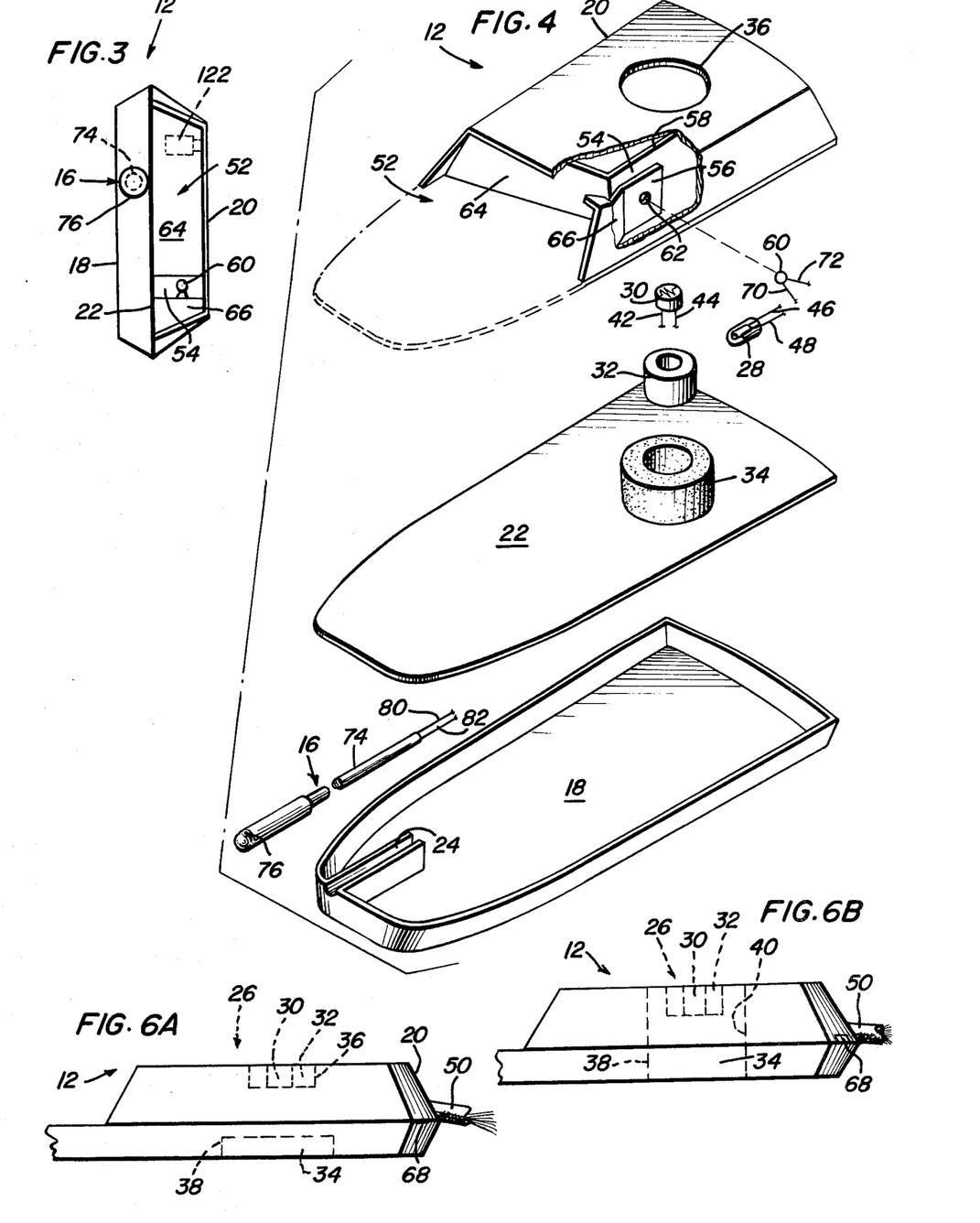
FIG. 3 is a front end view of the sensor of FIG. 1.
FIG. 4 is a perspective, exploded view of the sensor of FIG. 1.
FIG. 6A and 6B are side views of a portion of the sensor of FIG. 1 showing other embodiments for mounting the photoelectric pulse detector.

As shown in the alternative embodiments of FIGS. 6A and 6B, resilient material 34 can also be positioned to be contacted by the thumb or by both the finger and thumb. More specifically, as shown in FIG. 6A, photoelectric pulse detector 26 can be mounted directly in opening 36 in top 20 for association with the digit being monitored, and resilient material 34 mounted in opening 38 in base 18 so that it is positioned to be contacted by the thumb. Alternatively, resilient material 34 can extend through opening 40 in center plate 22 as shown in FIG. 6B so that the respective portions of housing 14 gripped by the finger and the thumb are both cushioned.

Photocell 30 is preferably a cadmium selenide photocell having opaque sides and bottom portions so that the photocell is shielded from the direct radiation from bulb 28 and is responsive only to radiation emanating from the patient's finger. Photocell 30 as well as radiation-transmitting ring 32 are preferably mounted so that they are flush with the top surface of top 20. Photocell 30 is selected to provide a maximum response to electromagnetic energy having a wave length near 7,350 angstroms. The commercially available Clairex type CL-903L photocell has been found to be satisfactory. In general, a photocell having a peak response between 7,100 and 7,500 angstroms is preferred since a peak response in this range substantially matches the radiated energy of bulb 28. Photocell 30 has leads 42 and 44 for appropriate electrical connection. Light bulb 28 is of conventional type and has power leads 46 and 48. A main cable 50 electrically connects sensor 12 with remote circuitry.

Opening 52 in housing 14 communicates with wind tunnel 54. Wind tunnel 54 is formed by two vertical plates 56 and 58 which extend in the longitudinal direction of sensor 12 and comprise a portion of top 20. Thermistor 60 is mounted in opening 62 in plate 56 so that it is positioned in wind tunnel 54. Expired air is directed into wind tunnel 54 by vertical plates 64 and 66 which converge toward wind tunnel 54 and comprise a portion of top 20. Vent slot 68 is provided in the rear portion of top 20 and provides an exit for expired air. Thermistor 60 has leads 70 and 72 for appropriate connection. Thermistor 60 is heated to a temperature above the temperature of the respiration air, typically about 115° F, by current flowing through the thermistor.

Thermistor 60 is typically a glass bead thermistor. Suitable commercially available thermistors are sold by Fenwal Electronics, Inc., Waltham, Massachusetts, under the designations GC32J1and GC32J2. The characteristics of these thermistors are described in Fenwal's Manual EMC-6. The glass provides moisture protection which is desirable since the thermistor is exposed to nasal exhalation.

Probe 16 comprises hollow shaft 74 and end cap 76 mounted on the end of the shaft. Thermistor 78 is soldered in the closed forward end of cap 76 and is connected to remote electrical circuitry through lead 80. Shaft 74 as shown in FIGS. 1-4 is formed from a flexible plastic, preferably polyurethane or nylon. Since shaft 74 is not electrically conductive, a second lead 82 is also connected to cap 76 at solder joint 84. The open rear end of cap 76 is sealed by plug 86 which typically comprises an epoxy sealer or room temperature vulcanizing silicone rubber which is impervious to moisture. Each of leads 80 and 82 extends through plug 86, hollow shaft 74 and into housing 14. In this embodiment, the exposed portion of probe 16 is typically about 2 inches long and end cap 76 about 1¼ inches long. Cap 76 typically comprises a nickel plated brass cylinder having a closed end and a 0.005 inch wall thickness. Thermistor 78 and leads 80 and 82 are soldered to cap 76 with a 60/40 solder.

Figure 1:
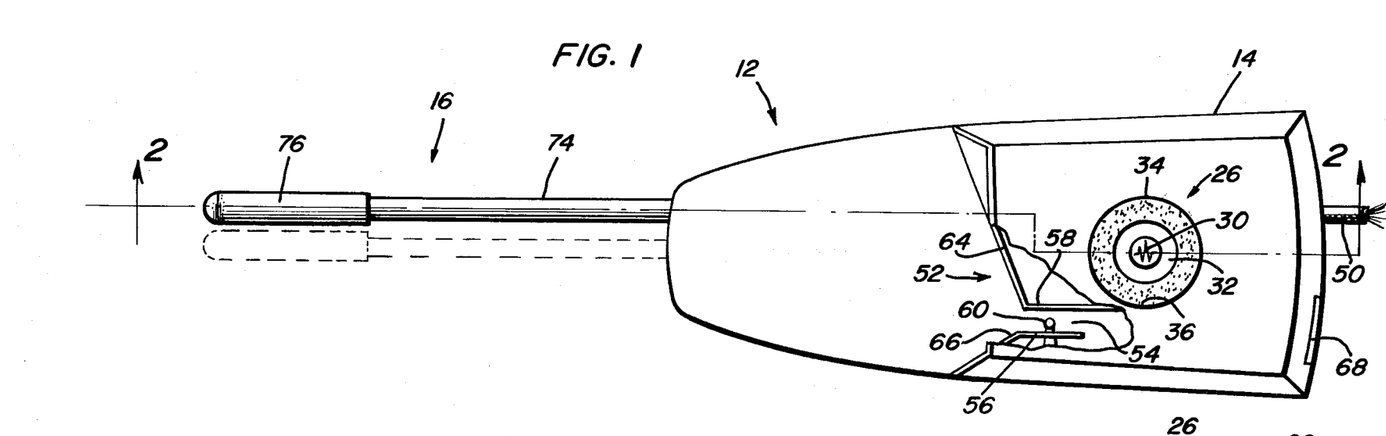
FIG. 1 is a plan view, partly in section, of the sensor of the present invention.
Figures 2, 5:
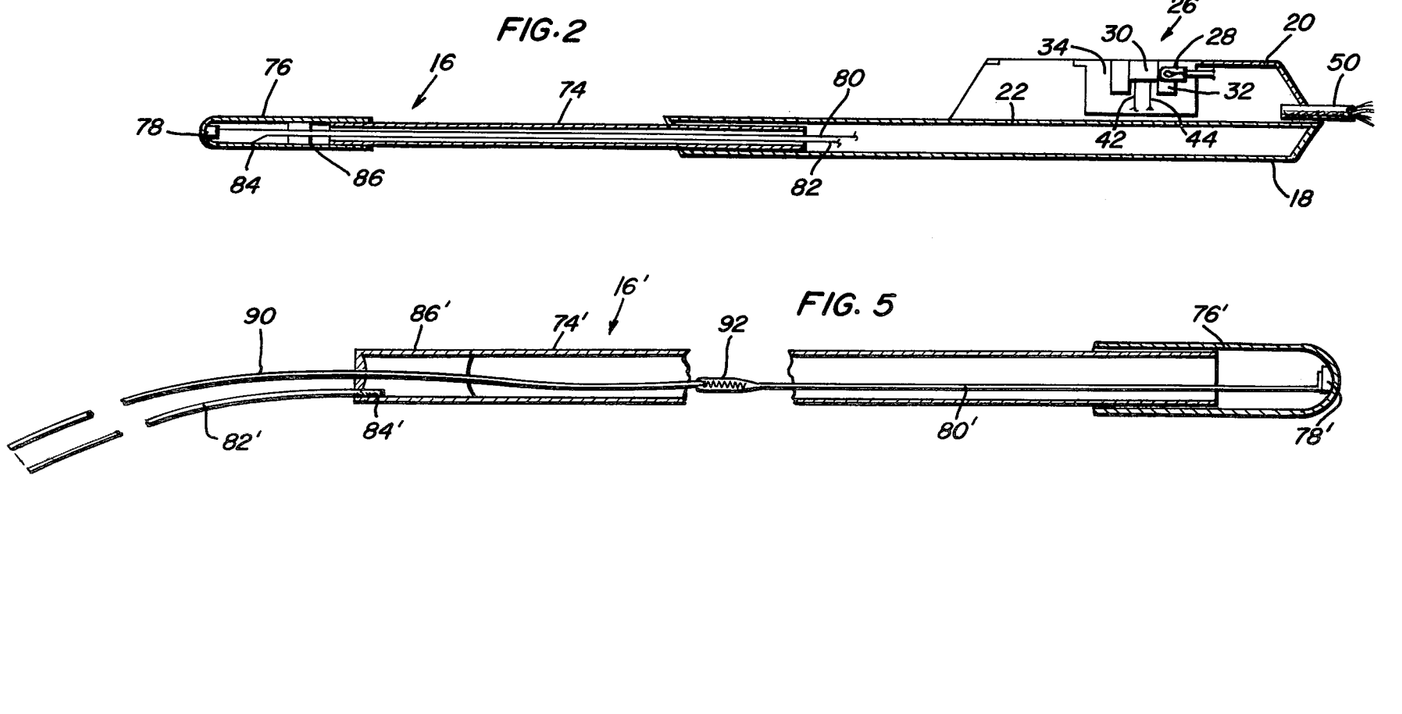
FIG. 2 is a vertical, cross-sectional view of the sensor taken along line 2—2 of FIG. 1.
FIG. 5 is a vertical, cross-sectional view of another embodiment of the probe of FIG. 1.

FIG. 5 shows an alternative embodiment of the probe in which shaft 74' is formed from metal such as stainless steel, typically, a tube having a wall thickness of 0.003 inch. The forward end of shaft 74' is soldered to cap 76' using a 60/40 solder. Lead 80' from thermistor 78' is insulated, typically a No. 40 coated wire, and is connected to an insulated wire 90, typically a No. 32 insulated wire, at insulating sleeve 92. In this embodiment, plug 86' is used to seal the rear end of shaft 74 rather than cap 76 as in the embodiment illustrated in FIGS. 1-4. Since metal shaft 74' is electrically conductive, lead 82' can be soldered to the rear end of shaft 74' rather than to cap 76'. In this embodiment, cap 76' comprises about ½ inch of the length of probe 16'.

Thermistor 78 can be any thermistor with suitable temperature response characteristics for sensing clinical temperature values. a suitable commercially available thermistor is the Type A thermistor sold by Fenwal Electronics, Inc., Waltham, Massachusetts. The characteristics of the Fenwal Type A thermistor are described in Fenwal's Manual EMC-6. Thermistor 78 is typically a 0.010 inch thick and 0.050 inch in diameter disc.

Figure 7:
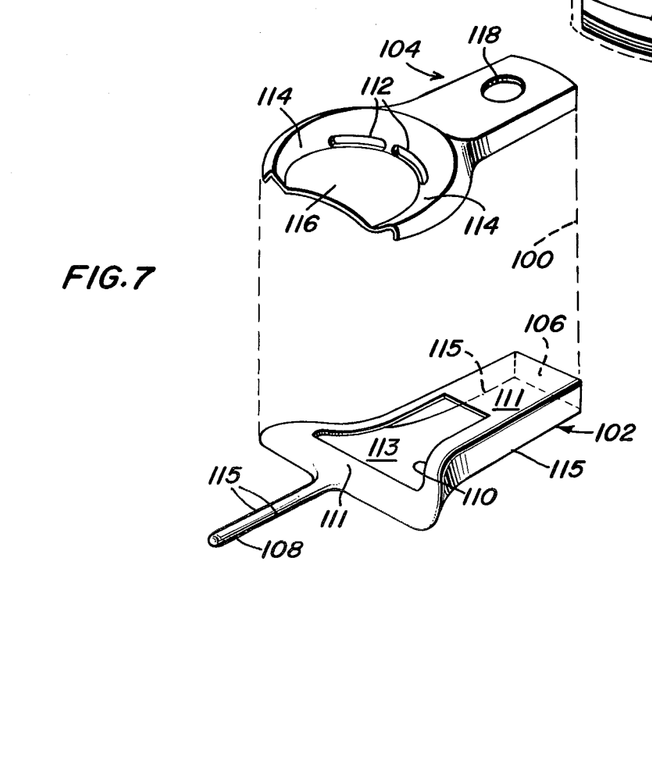
FIG. 7 is a perspective, exploded view of the disposable cover.
Figure 8:
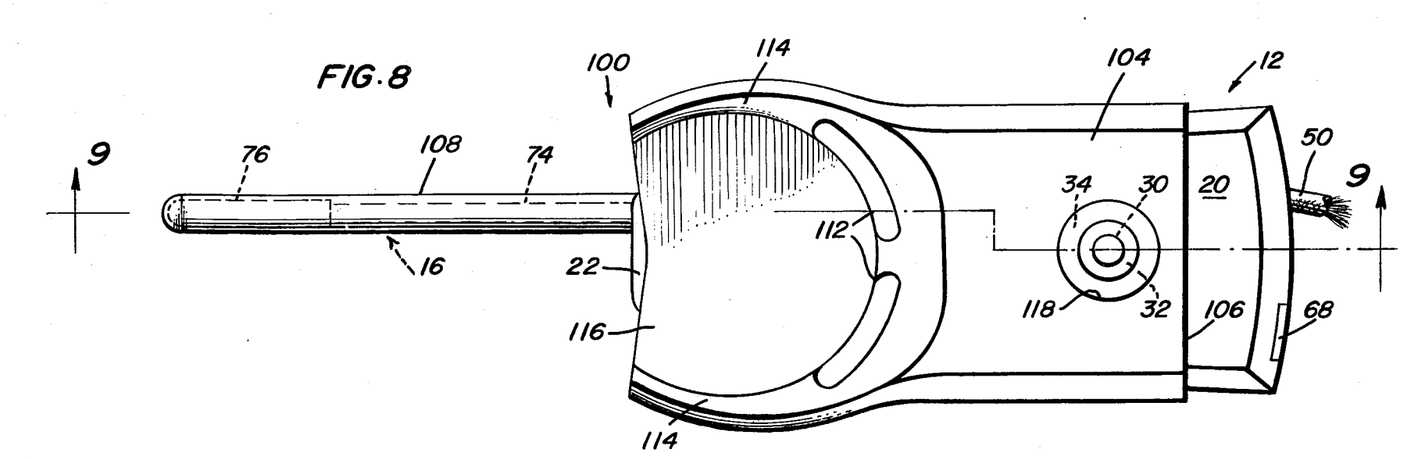
FIG. 8 is a plan view of the sensor of FIG. 1 associated with the disposable cover of FIG. 7.
Figures 9, 11:
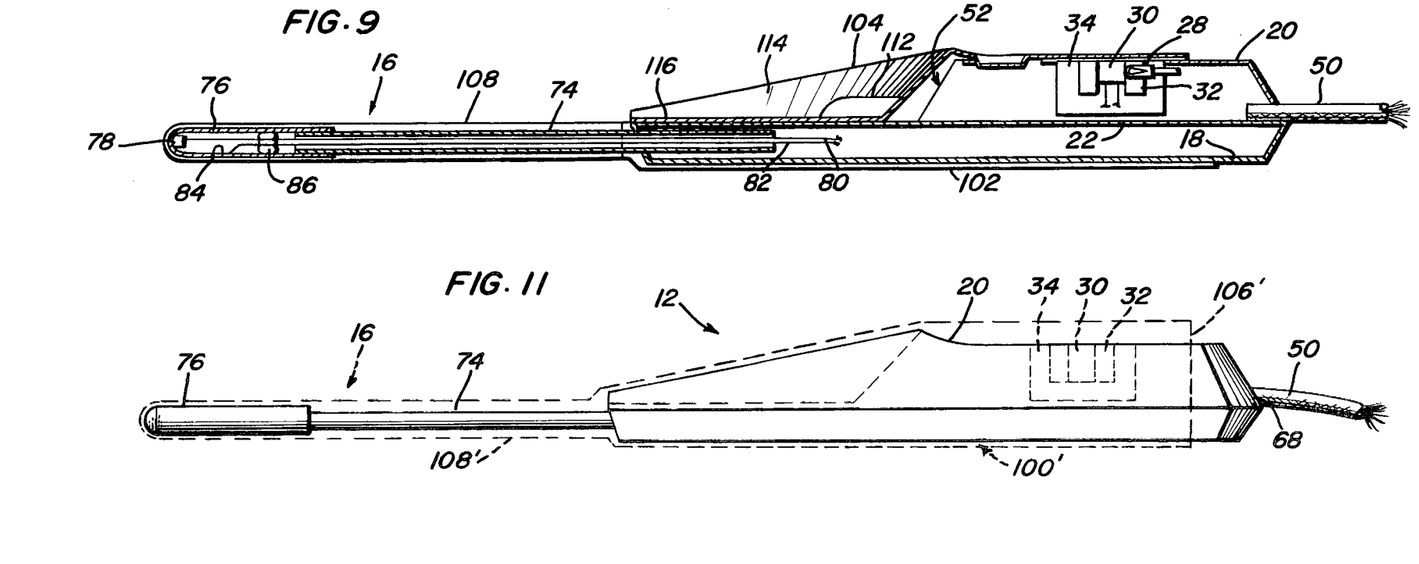
FIG. 9 is a vertical, cross-sectional view of the sensor and associated disposable cover taken along line 9—9 of FIG. 8.
FIG. 11 is a side view of the sensor and associated disposable cover of FIG. 10.

Referring now to FIGS. 7-9, the detector also comprises disposable cover 100. As best seen in FIG. 7, cover 100 basically comprises a flexible portion 102 and a rigid portion 104. Flexible portion 102 is formed from a thermoplastic film such as a 0.001 or 0.002 inch thick film formed from polyethylene or ethylene copolymerized with ethyl vinyl acetate or ethyl methyl acetate. A thin film is used so as to minimize the degradation of the thermal response time of the probe. Rigid portion 104 is formed from a relatively rigid thermoplastic sheet such as a 0.020 to 0.040 inch thick styrene or polypropylene sheet to which is fastened flexible portion 102 by heat sealing or adhesive. Flexible portion 102 is relatively good heat transmittor and rigid portion 104 is a relatively good heat insulator. Flexible portion 102 has opening 106 for sleeving over probe 16 and housing 14. Flexible portion 102 includes extension 108 which covers probe 16 and respiration opening 110 which allows respiration air to flow past thermistor 60 mounted in wind tunnel 54. The thermistor 60 responds only to the air flow at expiration. Flexible portion 102 is typically formed by heat sealing two appropriately shaped top and bottom pieces 111 and 113, respectively, of thermoplastic film together along side seams 115. The inside tip of extension 108 is preferably coated with a heat conducting fluid such as glycerin, light mineral oil, or a silicone fluid to increase the heat conductivity between disposable cover 100 and probe 16. Only sufficient heat conducting fluid should be used to wet the tip of extension 108 in order to provide the minimum heat capacity while maximizing the heat conductivity.

Rigid portion 104 has openings 112 which communicate with opening 110 in flexible portion 102. Respiration air is directed through openings 112 by saucer shaped side walls 114. Front end 116 of rigid portion 104 is substantially flat and is adapted to be contacted by the patient's lips. Rigid portion 104 also comprises opening 118 which is approximately the same size and shape as opening 36 in top 20 of housing 14. When disposable cover 100 is placed over sensor 12, opening 118 will be aligned with opening 36.

Figure 10:
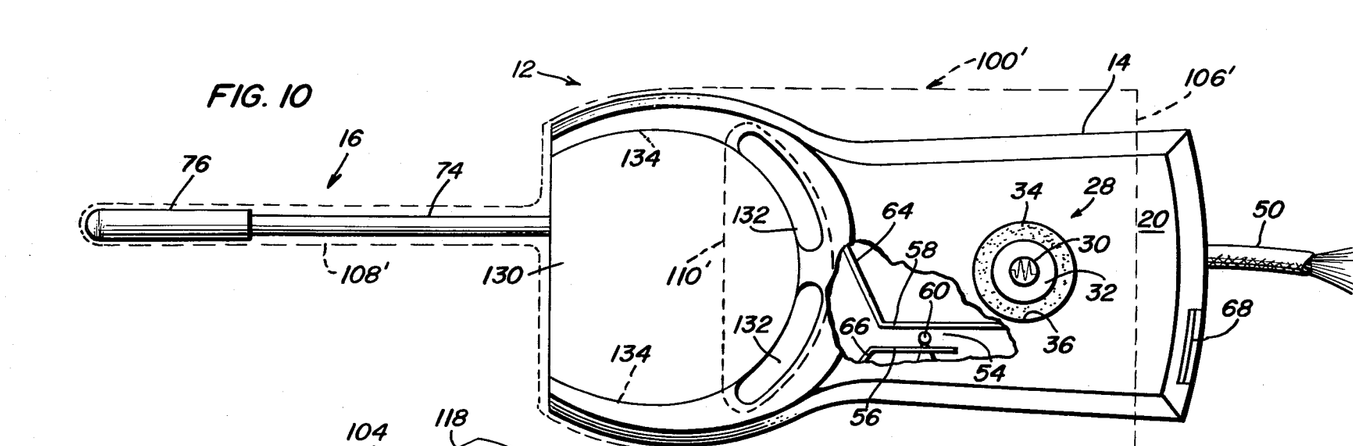
FIG. 10 is a plan view of another embodiment of the sensor of FIG. 1 associated with another embodiment of the disposable cover of FIG. 7 shown in dotted lines.
Figure 12:
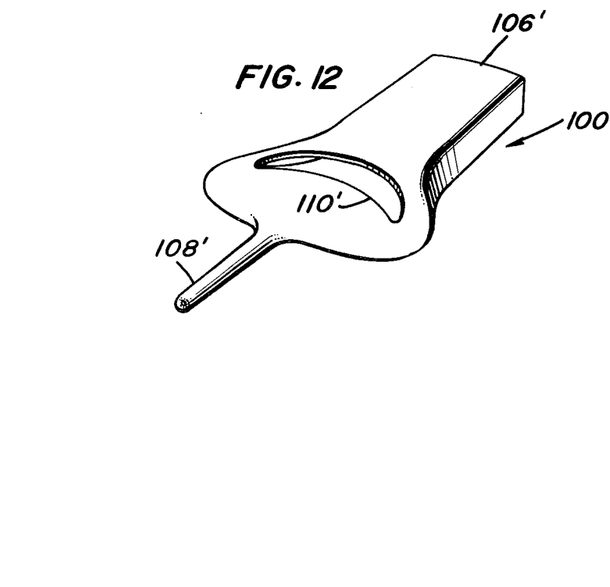
FIG. 12 is a perspective view of the disposable cover of FIG. 10.

FIGS. 10-12 show an alternative embodiment of the disposable cover and sensor. In this embodiment, disposable cover 100' consists of a 0.001 or 0.002 inch thick thermoplastic film. As in the embodiment shown in FIGS. 7-9, disposable cover 100' has opening 106' for sleeving over probe 16 and housing 14 and opening 110' for allowing respiratory air to contact thermistor 60 mounted in wind tunnel 54. In essence, disposable cover 110' is similar to flexible portion 102 in the embodiment shown in FIGS. 7-9 but opening 110 shown in FIG. 7 has a somewhat modified shape as shown at 110' in FIG. 10. In this arrangement, the front end of housing 14 acts to direct respiration air into wind tunnel 54 and provides rigid portion 130 for contacting the patient's lips. More specifically, top 20 of housing 14 has openings 132 into which respiration air is direction by saucer-shaped side walls 134. Openings 132 and side walls 134 are functionally equivalent to openings 112 and side walls 114, respectively, of rigid portion 104 in the embodiment of FIGS. 7-9.

The normal use of the detector will be described with particular reference to the embodiment described in FIGS. 1-4 and 7-9. Disposable cover 100 is sleeved over probe 16 and housing 14 so that opening 118 is aligned with opening 36. The patient then holds sensor 12 in his hand so that his finger is over photoelectric detector 26 and places probe 16 in his mouth, preferably with cap 76 well back under the tongue. In this position, the patient's lips contact front end 116 of disposable cover 100. The patient's temperature is directly sensed by temperature-sensing thermistor 78.

As the patient breathes through his nose, the nasal exhalations pass through openings 112 and 100 in disposable cover 100, through opening 52 and wind tunnel 54 in housing 14 and exit sensor 12 through vent hole 68. Self-heated thermistor 60 in wind tunnel 54 is cooled by the flow of expired air and the patient's respiration rate is derived by this periodic cooling of the thermistor.

The patient's pulse rate is derived from the changes in the light transmission characteristics of his finger sensed by photoelectric pulse detector 26. More specifically, radiation emitted by bulb 28 is modulated by the patient's finger and detected by photoelectric detector 30. The change in the radiation received by detector 30 is converted into a pulse rate reading.

Although the preferred embodiments of the present invention have been described herein, it should be appreciated that there are many modifications falling within the scope of the present invention. For example, it should be recognized that the detector can be used for sensing either temperature, respiration or pulse without simultaneously detecting the other body functions. Additionally, although a preferred shape for the disposable cover and sensor have been described, it should be recognized that different configurations can be used within the scope of the present invention. For example, the sensor could be proportioned to detect rectal temperature and pulse. In this case the photoelectric pulse detector would sense changes in the radiation transmission characteristics of the tissue of the buttocks adjacent to the rectum. Accordingly, the present invention should not be limited by the above, but should be limited only as defined in the appended claims.

We claim:

1. An apparatus for sensing temperature, pulse and respiration comprising a housing and a probe extending from said housing so that when the probe is placed in a patient's mouth the patient's lips are adapted to contact at least a portion of the housing, temperature sensor means mounted on said probe for insertion into the mouth, photoelectric pulse sensor means mounted on said housing and positioned to be contacted by tissue through which blood is circulating, respiration sensor means mounted in said housing and positioned to be in the path of nasal air flow when said probe is inserted into the mouth, said housing having an opening for exposing said respiration sensor means to said nasal air flow, and a disposable cover for removably covering said probe and at least a portion of said housing comprising a radiation-transmitting portion adapted to associate with said photoelectric pulse sensor means and an opening adapted to associate with said respiration sensor means.

2. The apparatus of claim 1 in which said temperature sensor means and said respiration sensor means each comprise a thermistor.

3. The apparatus of claim 2 and further including means for passing a current through said respiration sensor thermistor to heat said thermistor to a temperature above the temperature of said nasal air.

4. The apparatus of claim 1 in which said housing includes a wind tunnel and said respiration sensor means comprises a thermistor mounted in said wind tunnel.

5. The apparatus of claim 4 in which said opening for exposing said respiration sensor means to said nasal air flow is defined by first and second wall means which converge toward said wind tunnel.

6. The apparatus of claim 1 in which said photoelectric pulse sensor means comprises means for emitting radiation and photocell means for receiving radiation emanating from said tissue.

7. The apparatus of claim 6 in which said photoelectric pulse sensor means further comprises radiation transmitting means associated with said radiation emitting means.

8. The apparatus of claim 1 in which said probe comprises a hollow shaft and a heat-transmitting cap attached to one end of said shaft, said temperature sensor means being mounted in said heat-transmitting cap.

9. The apparatus of claim 8 in which said hollow shaft is composed of a flexible plastic.

10. The apparatus of claim 8 in which said hollow shaft is composed of metal.

11. The apparatus of claim 8 in which said probe includes moisture-impervious means positioned between said temperature sensor means and the other end of said shaft.

12. The apparatus of claim 11 in which said moisture-impervious means comprises an epoxy or a room temperature vulcanizing silicone rubber.

13. The apparatus of claim 1 in which, said housing has cushioning means positioned to be contacted by the hand of a patient so that the flow of blood circulating through said tissue is not restricted.

14. The apparatus of claim 1 in which said disposable cover comprises a flexible sheath for said apparatus.

15. The apparatus of claim 1 in which said disposable cover comprises a sheath for said apparatus and which has a flexible portion and a rigid portion.

16. The apparatus of claim 1 in which said disposable cover further comprises means for directing nasal air flow to said respiration detection means.

17. An apparatus for sensing body temperature and respiration comprising a housing, a probe attached to said housing, temperature sensor means mounted on said probe for insertion into the mouth, respiration sensor means mounted in a wind tunnel in said housing, an opening in said housing for exposing said respiration sensor means to nasal air flow when said probe is inserted into the mouth, said opening for exposing said respiration sensor means to said nasal air flow being defined by first and second wall means which converge toward said wind tunnel, and a disposable cover for removably covering said probe and at least a portion of said housing comprising an opening adapted to associated with said opening in said housing.

18. The apparatus of claim 17 in which said temperature sensor means and said respiration sensor means each comprise a thermistor.

19. The apparatus of claim 18 and further including means for passing a current through said respiration sensor thermistor to heat said thermistor to a temperature above the temperature of said nasal air.

20. The apparatus of claim 17 in which said respiration sensor means comprises a thermistor mounted in said wind tunnel.

21. The apparatus of claim 16 in which said apparatus further comprises means for directing said nasal air flow through said opening in said housing.

22. The apparatus of claim 16 in which said probe comprises a hollow shaft and a heat-transmitting cap attached to one end of said shaft, said temperature sensing means being mounted in said heat-transmitting cap.

23. The apparatus of claim 22 in which said hollow shaft is composed of a flexible plastic.

24. The apparatus of claim 22 in which said hollow shaft is composed of metal.

25. An apparatus for sensing temperature and respiration comprising a housing and a probe extending from said housing, temperature sensor means mounted on said probe for insertion into the mouth, respiration sensor means mounted in said housing, means associated with said housing for directing nasal air flow to said respiration sensor means when said probe is inserted into the mouth, and a disposable cover for removably covering said probe and at least a portion of said housing comprising an opening attached to associate with said respiration sensor means.

26. The apparatus of claim 25 in which the disposable cover has a heat-transmitting portion for covering said temperature sensor.

27. The apparatus of claim 25 in which said cover includes a portion covering and cooperating with said nasal air flow directing means.

28. An apparatus for sensing temperature and respiration comprising a housing and a probe extending from said housing, temperature sensor means mounted on said probe for insertion into the mouth, respiration sensor means mounted in a wind tunnel in said housing and positioned to be in the path of nasal air flow when said probe is inserted into the mouth, said housing having an opening for exposing said respiration sensor means to said nasal air flow, said opening for exposing said respiration sensor means to said nasal air flow being defined by first and second wall means which converge toward said wind tunnel, and a disposable cover for removably covering said probe and at least a portion of said housing comprising an opening attached to associate with said opening in said housing.

29. The apparatus of claim 28 in which respiration and temperature sensor means comprise a thermistor.

30. The apparatus of claim 29 and further including means for passing a current through said respiration sensor thermistor to heat said thermistor to a temperature above the temperature of said nasal air.

31. The apparatus of claim 28 in which said probe comprises a hollow shaft and a heat-transmitting cap attached to one end of said shaft, said temperature sensor means being mounted in said heat-transmitting cap.

32. The apparatus of claim 31 in which said hollow shaft is composed of a flexible plastic.

33. The apparatus of claim 31 in which said hollow shaft is composed of metal.

34. An apparatus for sensing temperature and respiration rate comprising a housing, an elongate probe and an intermediate section connected at one side to said housing and at another side to said probe, said probe extending from the side of said intermediate connecting section which is remote from said housing, a temperature sensor mounted in the end of said probe remote from said intermediate connecting section, said housing having an interior defining a wind tunnel, a respiration sensor mounted in said wind tunnel, said housing defining an inlet opening communicating with the upstream end of said wind tunnel and an outlet opening communicating with the downstream end of said wind tunnel, said probe being dimensioned such that when it is inserted into a patient's mouth it is entirely contained within the patient's mouth and the patient's lips engage said intermediate connecting section, said intermediate connectingg section having a non-circular cross-section having a major axis and a minor axis, the width of said non-circular cross-section along said major axis being substantially greater than the width of said non-circular cross-section along said minor axis whereby said major axis is oriented parallel to the line of joining of the patient's lips when said probe is inserted in the patient's mouth and the intermediate connecting section is engaged by the patient's lips so that the apparatus can be firmly held by the patient in a fixed non-rotating manner relative to the longitudinal axis of the apparatus to enable proper positioning of said inlet opening in relation to the patient's expired nasal air flow.

35. A disposable cover for use in combination with an apparatus for sensing temperature and respiration rate having a housing, an elongate probe and an intermediate section connected at one side to said housing and at another side to side probe, said probe extending from the side of said intermediate connecting section which is remote from said housing, a temperature sensor mounted in the end of said probe remote from said intermediate connecting section, said housing having an interior defining a wind tunnel, a respiration sensor mounted in said wind tunnel, said housing defining an inlet opening communicating with the upstream end of said wind tunnel and an outlet opening communicating with the downstream end of said wind tunnel, said probe being dimensioned such that when it is inserted into a patient's mouth it is entirely contained within the patient's mouth and the patient's lips engage said intermediate connecting section, said intermediate connecting section having a non-circular cross-section having a major axis and a minor axis, the width of said non-circular cross-section along said major axis being substantially greater than the width of said non-circular cross-section along said minor axis whereby said major axis is oriented parallel to the line of joining of the patient's lips when said probe is inserted in the patient's mouth and the intermediate connecting section is engaged by the patient's lips so that the apparatus can be firmly held by the patient in a fixed non-rotating manner relative to the longitudinal axis of the apparatus to enable proper positioning of said inlet opening in relation to the patient's expired nasal air flow, said disposable cover comprising means for removably covering said apparatus including said probe and at least a portion of said housing and an opening adapted to associate with said inlet opening defined by said housing to allow expired nasal air flow to flow through said wind tunnel.

36. The cover of claim 35, in which said cover further comprises a relatively good heat-transmitting portion for covering said temperature sensor.

* * * * *

UNITED STATES PATENT AND TRADEMARK OFFICE
CERTIFICATE OF CORRECTION

PATENT NO. : 4,036,211

DATED : July 19, 1977

INVENTOR(S) : Veth et al

It is certified that error appears in the above-identified patent and that said Letters Patent are hereby corrected as shown below:

Claim 25, line 10, "attached" should be -- adapted --;

Claim 28, line 14, "attached" should be -- adapted --;

Claim 34, line 18, "connectingg" should be -- connecting --.

Signed and Sealed this

Twentieth Day of December 1977

[SEAL]

Attest:

RUTH C. MASON
Attesting Officer

LUTRELLE F. PARKER
Acting Commissioner of Patents and Trademarks